(12) United States Patent
Wilk et al.

(10) Patent No.: US 6,199,555 B1
(45) Date of Patent: Mar. 13, 2001

(54) CANCER TREATMENT METHOD

(76) Inventors: Peter J. Wilk, 185 West End Ave., New York, NY (US) 10023; R. Neil Sudol, P.O. Box 664, Scarsdale, NY (US) 10583

( * ) Notice: Subject to any disclaimer, the term of this patent is extended or adjusted under 35 U.S.C. 154(b) by 0 days.

(21) Appl. No.: 09/071,430

(22) Filed: May 1, 1998

(51) Int. Cl.⁷ .................................................. A61B 19/00
(52) U.S. Cl. ........................................................ 128/898
(58) Field of Search ............................................ 128/898

(56) References Cited

PUBLICATIONS

Ogawa, J., Surgical treatment of pulmonary metastases from digestive organs and management of malignant pleural effusions, Nippon Geka Gakkai zasshi, 100 (2), p. 216–9, Feb. 1999, Abstract.*

Lee KA, Harvey JC, Reich H, Beattie EJ, Management of malignant pleural effusions with pleuroperitoneal shunting, Journal of the American College of Surgeons, 178 (6) p. 586–8, Jun. 1994, Abstract.*

Lynch TJ Jr, Management of malignant pleural effusions, Chest, 103 (4 Suppl), p. 385S–389S, Apr. 1993, Abstract.*

Logan SE, Morton DL, An analytical model for intra–arterial versus intravenous infusion of Adriamycin, Biomedical sciences instrumentation, 25 p. 239–46, 1989, Abstract.*

Bouvier G, Penn RD, Kroin JS, Beigque R, Guerard MJ, Direct delivery of medication into a brain tumor through multiple chronically implanted catheters, Neurosurgery, 20 (2) p. 286–91, Feb. 1987, Abstract.*

New Scientist, Drug delivery combats brain tumor, New Scientist, Sep. 1987, p. 34, Abstract.*

* cited by examiner

Primary Examiner—Dinh X. Nguyen
(74) Attorney, Agent, or Firm—R. Neil Sudol; Henry D. Coleman

(57) ABSTRACT

In a method for treating cancer, a tube is inserted into a patient, so that a distal end of the tube is disposed proximately to a tumor. A sclerosing agent such as a concentrated sugar solution is then fed through the tube into the patient and into the tumor. The tube can take the form of a catheter which is introduced into the patient through the patient's vascular system.

23 Claims, 3 Drawing Sheets

CANCER TREATMENT METHOD

BACKGROUND OF THE INVENTION

This invention relates to a method for the treatment of cancer. More particularly, this invention relates to a method for the destruction of tumors. Even more particularly, this invention relates to a minimally invasive method for the destruction of tumors.

Cancer continues to be a scourge of mankind. There is a plethora of techniques for treating cancer. Most of these techniques have dire side effects, generally involving substantial amounts of pain to the patient.

Once cancer has reached the tumor stage, where lumps of cancerous tissues are detectable either directly through touch and vision or indirectly with the aid of MRI and CAT scanners, the principal treatment is surgical. The victim is operated on and the tumor cut out of the body. Frequently, the location and size of the tumor are such that surgical removal results in a severe impairment to the patient's body and lifestyle. For example, surgical removal of a large tumor in a femur frequently results in an amputation.

The operations for surgically removing tumors are nearly universally open incision type operations. These operations are naturally debilitating and require extensive post surgical care. For these reasons, the costs of conventional open incision surgery are enormous.

Although minimally invasive procedures such as laparoscopic or thoracoscopic surgery have increased at geometric rates in frequency of performance, minimally invasive surgery for the treatment of cancer has not been employed. Of course, other kinds of minimally invasive techniques such as chemotherapy and radiation treatment are widely practiced. However, these techniques have substantial debilitating side effects. Patients must suffer significantly in virtually every case.

Nevertheless, minimally invasive techniques are the future of medicine. Patient trauma and hospitalization time are reduced. In addition, costs and expenses are decreased.

OBJECTS OF THE INVENTION

An object of the present invention is to provide a method for treating cancer.

A further object of the present invention is to provide a method for destroying tumors.

It is a more specific object of the present invention to provide a method for destroying tumors which is less invasive than conventional open-incision surgical techniques.

It is another object of the present invention to provide such a method which is less expensive than conventional techniques.

A further object of the present Invention is to provide a cancer treatment technique which is minimally detrimental to the patient.

These and other objects of the present invention will be apparent from the drawings and descriptions herein.

SUMMARY OF THE INVENTION

The present invention arises from the applicant's familiarity with patients who, after surgery, are incapable of eating. Such patients require enormous amounts of energy, more than healthy individuals, in order to assist the healing process. These patients are conventionally supplied with the necessary energy and nutrients in the form of a highly concentrated sugar solution, known as total parenteral nutrition, delivered via a catheter inserted into the vena cava. It is well known that such a solution is not fed to small veins because it is sclerotic. Small veins are destroyed by highly concentrated sugar solutions.

The present invention is based on this known sclerotic effect of highly concentrated sugar solutions and on the documented fact that tumors grow their own blood supplies in order to support their abnormally pronounced cellular activity. The present invention contemplates the purposeful delivery of a highly concentrated sugar solution to the blood supply system of a tumor, either directly through the patient's vascular system or indirectly through the body of the tumor. Because of the known sclerotic effect of concentrated sugar solutions, the blood supply system and more specifically the venous side of the tumor blood supply system collapses and ceases its function. With its blood supply suddenly and irreversibly blocked, the tumor is soon destroyed. If necessary, the destroyed tumor can be removed by conventional surgical techniques after the cells have died in the patient.

A method for treating cancer comprises, in accordance with the present invention, the steps of inserting a tube into a patient, so that a distal end of the tube is disposed proximately to a tumor, and feeding a sclerosing agent through the tube into the patient and into the tumor. The word "distal" is used herein relative to a radiologist or other medical personnel. Thus the distal end of a catheter is disposed inside a patient, away from the radiologist.

The sclerosing agent is preferably a concentrated sugar solution, for example, a 25–50% dextrose solution. However, other known sclerotic agents can be used. For example, 5% quinine and urea hydrochloride solution. Preferably, the sclerotic agent is a natural substance which is generally nontoxic and biocompatible. A sugar such as dextrose is such a substance. However, the sclerosing procedure of the present invention may be combined with other kinds of treatment which include the introduction of toxic substances into the body. For example, an alcohol such as methyl alcohol or arsenic may be delivered to the body of the tumor for selective absorption into cancer cells.

In many cases, the tube which is used to deliver the sclerosing agent to the tumor can take the form of a catheter which is introduced into the patient through the patient's vascular system. The catheter is inserted along blood vessels until the distal end of the catheter is proximate to the tumor. Preferably, the catheter is inserted from the upstream side (through arteries) so that the distal end of the catheter is disposed near the tumor, in an artery supplying the tumor.

Pursuant to another feature of the present invention, the sugar is introduced into the catheter in a form which inhibits adherence of the sugar to an inner surface of the catheter. This procedure thus contemplates that the sugar is provided in the form of time release capsules or pellets which disintegrate upon entering the blood. Many controlled release delivery systems are known which would be suitable for purposes of the present invention.

Alternatively or additionally, the tube through which the sclerosing agent is introduced is provided with heating elements which heat the solution containing the sclerosing agent. Where the sclerosing agent is a concentrated sugar solution, the heating of the introducer tube reduces the precipitation of sugar along the lumen of the tube. Where the sclerosing agent is delivered in the form of time-release capsules or pellets, the heating of the introducer tube, particularly at a distal end thereof, accelerates the release of the sclerosing agent into solution and, more specifically, into the blood stream.

The heating of the introducer tube has an additional effect. It is known that heating (or cooling) of a tumor detrimentally affects the cellular activity of the tumor and may in itself destroy the tumor. In the prior art, this heating (or cooling) is generally accomplished by heating (or cooling) the entire patient. The tumor cells are more susceptible to the heating (or cooling) than are normal cells. In accordance with the present invention, the heating of a tumor is accomplished by feeding a heated solution directly to the tumor via a tube inserted either through the patient's vascular system or through overlying tissues. Where the solution contains a sclerotic agent, the necrotic effect on the tumor is enhanced.

The timed or delayed release of sugar or other sclerotic agent into solution may be accomplished by conventional means, for example, by coating of the sugar with a layer of a substance with dissolves in water at a controlled rate. As an alternative to time release coatings, the sugar may be fed to the introducer tube in the form of solid sugar pellets which are hardened throughout. The sugar dissolves in the blood supply of the tumor to produce a high sugar concentration, which results in a sclerosing of the tumor's blood supply system, particularly the venous portion thereof It is believed that the small veins of a tumor scierose in a sequential process.

In accordance with a further feature of the present invention, the sclerotic effect of the highly concentrated sugar solution is enhanced if the solution contains a vaso-constrictive agent such as nicotine or caffeine.

A method for treating cancer in accordance with the present invention serves to destroy tumors and is less invasive than conventional open-incision surgical techniques. The method uses inexpensive materials (catheters, drip feed apparatus, sugar solution), is easy to administer, and is substantially less toxic and debilitating to patients than other techniques.

DESCRIPTION OF THE PREFERRED EMBODIMENTS

Figure 1:
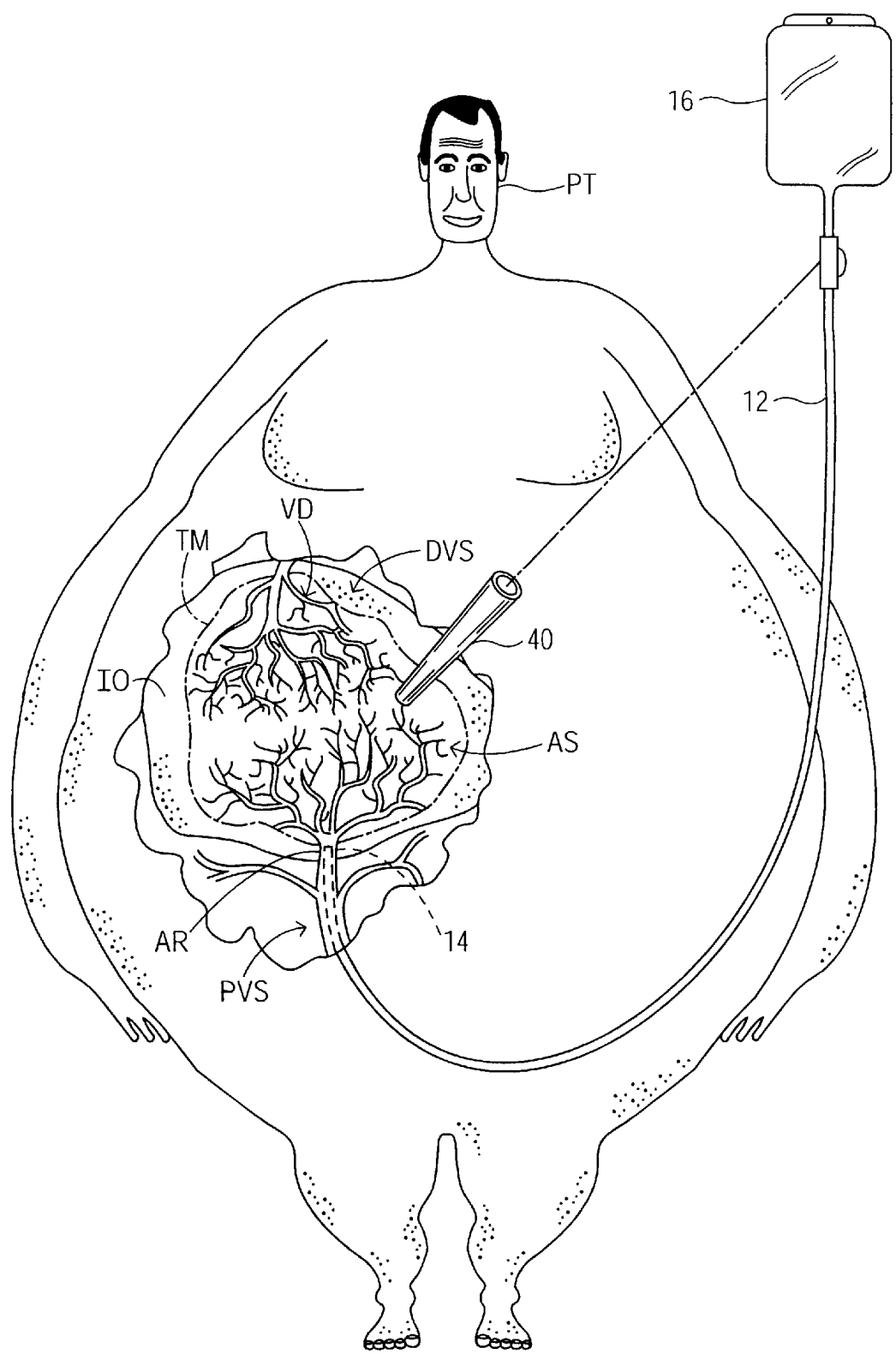
FIG. 1 is a schematic fish-eye-lens plan view of a patient, partially broken away, showing insertion of a catheter into the patient's vascular system in a cancer treatment method in accordance with the present invention.

As illustrated in the drawing, a tumor TM in an internal organ IO of a patient PT is supplied with blood via a dedicated vascular system DVS including an arterial supply AS and venous drainage VD. This dedicated vascular system DVS grows as the tumor TM grows. In order to treat the cancer and particularly destroy the tumor TM, a catheter 12 is inserted in a radiological procedure through the patient's vascular system PVS towards tumor TM. The insertion of catheter 12 continues until a tip 14 of the catheter is located near tumor TM, in an artery AR of the tumor's arterial system AS. At an opposite end (outside the patient), catheter 12 is connected to a reservoir 16 of a solution containing a sclerosing agent, such as a 25–50% concentration of a sugar such as dextrose.

It is well known that such a concentrated sugar solution, if fed to a small vein, will sclerose the vein. Such concentrated sugar solutions are routinely fed to people who have just undergone surgery or are otherwise unable to process food in their digestive tracts. These concentrated sugar solutions, which also contain other nutritive ingredients, are known as total parenteral nutrition and are supplied to a patient through a catheter extending through the upper chest and into the superior (or inferior) vena cava. It is only such a large vein that can receive a concentrated sugar solution without becoming inflamed and collapsing.

In the instant treatment procedure, the concentrated sugar solution from reservoir 16 is fed through catheter 12 at a rate controlled by a flow rate control member 18. The concentrated solution enters arterial supply AS of tumor TM and is pushed by arterial pressure into the capillaries of the tumor. The highly concentrated sugar solution has its known and expected effect on the capillaries and small veins SV of the venous drainage system VD of tumor TM. The small veins sclerose and cut off the flow of blood from the tumor. Eventually, in a relatively short time, the entire venous drainage system VD is closed down and concomitantly blood flow through the dedicated vascular system DVS of the tumor TM terminates. With the tumor's oxygen supply blocked, the cancerous cells die and the tumor is destroyed. The destroyed tumor may be subsequently removed by conventional, or minimally invasive, surgery.

Where the tumor to be treated is a large tumor, for example, between three and four centimeters in diameter, a 50% dextrose solution is fed to the tumor at a rate of 0.1–3 cc/minute (approximately 1 to approximately 30 drops/ minute). Where the sclerotic agent is a 25% dextrose solution, the feed rate may be increased. It is to be noted, however, that a precise rate need not be fixed in advance. A slow feed rate for the sclerotic sugar solution merely increases the time required to shut down the tumor's dedicated vascular system DVS. Once the veins are closed, they remain closed. Moreover, if the feed rate of the sclerotic sugar solution exceeds a minimum rate required for eradication of a selected tumor, the excess sugar either crystallizes in the tumor or is absorbed by the body. In either case, there is no detrimental effect on the patient. Of course, the feed rate of the sclerotic sugar solution should be a fraction of the total flow rate for the tumor's dedicated vascular system DVS. Feed rates (50% dextrose solution) of approximately 0.5% to approximately 5% of the flow rate of tumor's arterial system AS are in a preferred range for implementing the present tumor treatment method. However, rates between 0.1% and 10% can also be effective.

The sclerotic effect can be enhanced or accelerated by adding, to the sugar solution, an effective amount of a vaso-constrictive chemical or composition such as nicotine or caffeine. Effective amounts of these chemicals are notoriously well known.

Figure 2:
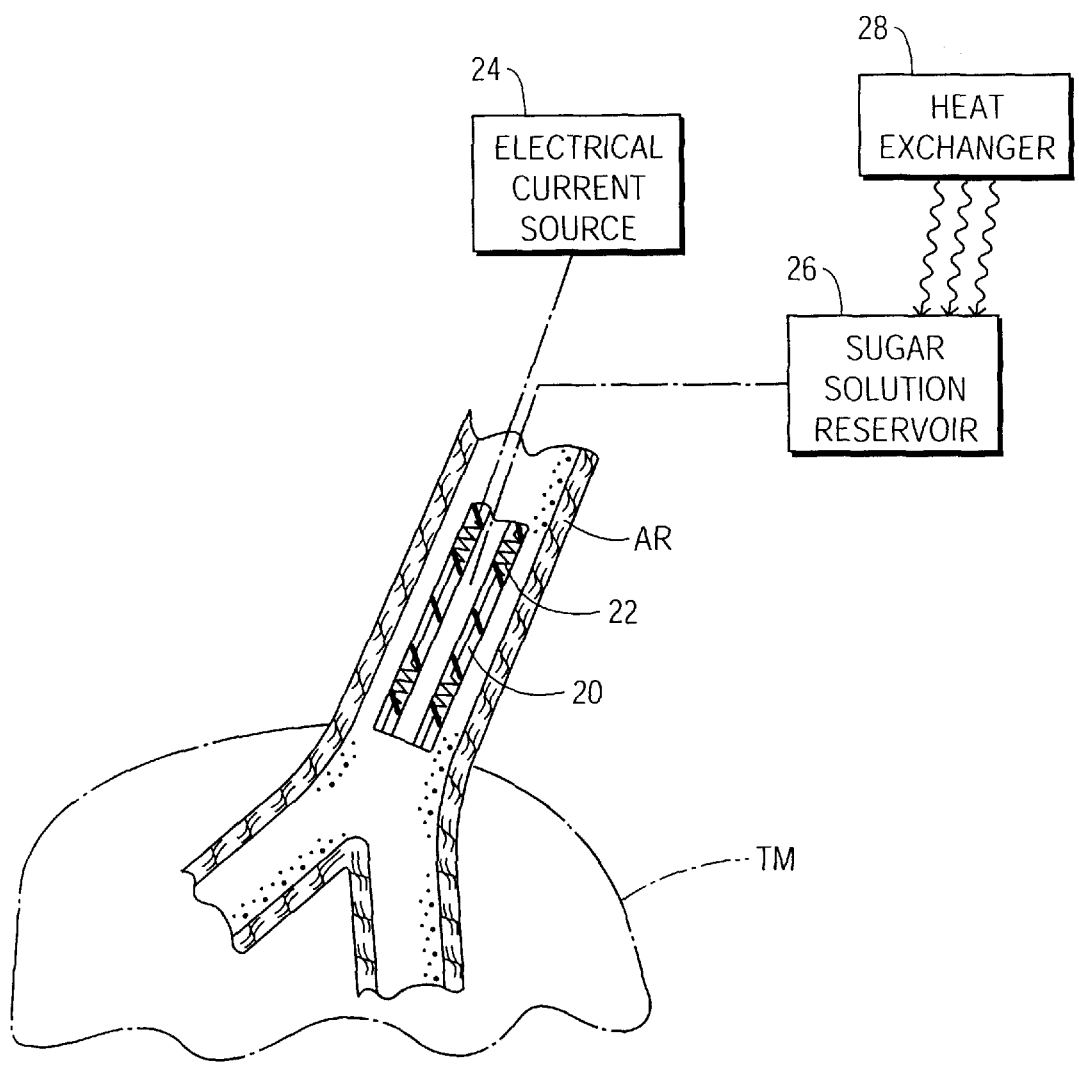
FIG. 2 is a diagram showing another catheterization of a patient in a cancer treatment method in accordance with the present invention.

During the delivery of a highly concentrated sugar solution through a catheter 12 to a tumor TM, sugar molecules precipitate out of solution and coat the inner surface or lumen of the catheter. Eventually, the deposited sugar layer effectively blocks the catheter and prevents delivery of further sclerosing solution. Various methods are useful for overcoming this problem. One obvious method is to remove catheter 12 and insert a replacement catheter. In another approach, depicted in FIG. 2, a catheter 20 is provided essentially along its length with resistance elements 22 which are connected to a source of electrical current 24. During the transfer of concentrated sugar solution from a reservoir 26 through catheter 20 to an arterial system AS of a tumor TM, current is supplied to resistance elements 22 to heat the catheter. Reservoir 24 may also be heated via a heat exchanger 28. The heating of catheter 20 and reservoir 26 serves in part to maintain sugar molecules in solution.

The heating of the sclerosing solution has an added effect of increasing the temperature of tumor TM, which is known to have a disruptive effect of tumor metabolism. In fact, it is a conventional cancer treatment to subject a patient to elevated temperatures. The normal cells of the patient are able to tolerate increased temperatures of a level which causes tumors to degenerate. The present method for heat treating a tumor is considered to be more effective and beneficial to the patient in that the tumor is targeted specifically. This enables higher temperatures to be applied to a tumor without causing the patient discomfort from the elevated temperatures.

It is to be noted that this targeted heating of a tumor could be used with a nonsclerotic saline solution. Moreover, this same treatment, with a sclerotic or nonsclerotic solution as the delivery medium, could be used to lower the temperature of a tumor for purposes of destroying the tumor. A catheter for heating or cooling is disclosed in U.S. Pat. No. 5,260,020 to Wilk and Tiefenbrun, the disclosure of which is hereby incorporated by reference. Although that reference is directed to sterilizing the inserted portion of an indwelling catheter and accordingly discloses heating only the inserted portion of the catheter, heating the entire catheter is a straightforward extension of the teachings of the reference.

Figure 4:
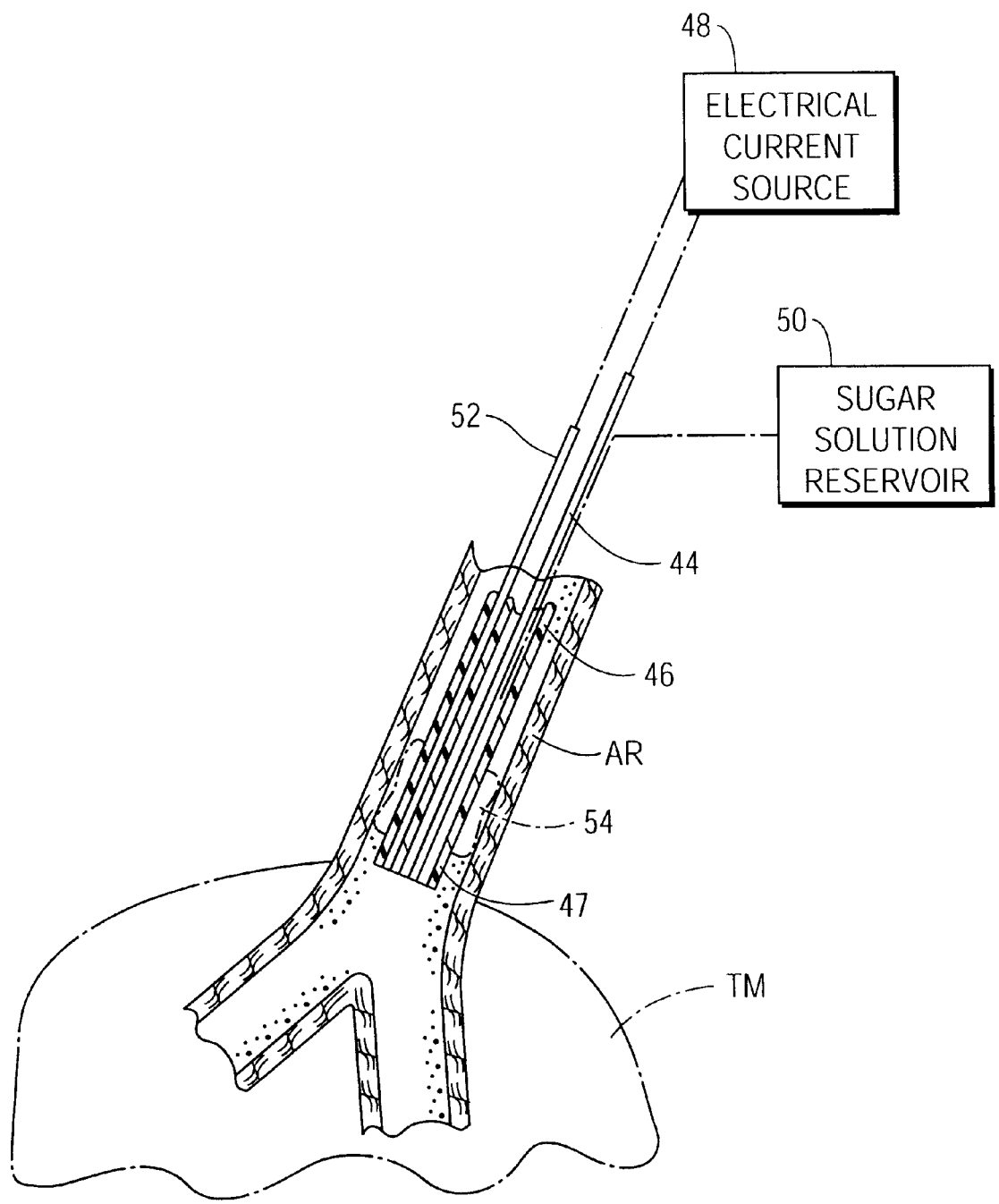
FIG. 4 is a diagram showing a catheterization of a patient in another cancer treatment procedure in accordance with the present invention.

In a modification of this technique depicted in FIG. 4, a wire obturator 44 inserted through a catheter 46 is connected to an electrical current source 48. Catheter 46 is inserted into the vascular system of a patient and guided to the tumor TM so that a distal or downstrean end 47 of the catheter is located in tumor artery AR. The transmission of electrical current through wire obturator 44 causes resistive heating and elevates the temperature of the wire, as well as the temperature of a concentrated sugar solution flowing through catheter 46 from a supply or reservoir 50. In order to complete a circuit, wire obturator 44 is connected at a downstream end of catheter 46 to another wire 52 embedded in or disposed along the outer side of catheter 46. It is contemplated that the wire obturator 44 is inserted periodically into catheter 46 to clear the catheter of sugar deposits. Alternatively, the wire may be left permanently in place during a procedure, provided that the lumen of catheter 46 is large enough and the diameter of wire obturator 44 small enough to allow the passage of the sclerosing solution. These dimensions in turn are controlled by the location and size of the artery AR into which the catheter is inserted.

Another method for solving the problem of sugar precipitation relies on a change in the form of the sugar being delivered through catheter 12. The sugar is provided in the form of microscopic particles or pellets encapsulated in a delay release coating. Such encapsulated sugar particles are disclosed in U.S. Pat. No. 5,536,156 to Fox et al., the disclosure of which is hereby incorporated by reference. Pursuant to the teachings of Fox et al., sucrose, glucose, lactose, and other sugars are coated with a food or pharmaceutical grade coating such as stearic acid, hydrogenated or partially hydrogenated oils, such as cottonseed, soybean, or rape seed oil, calcium stearate, stearyl alcohol or the like. Generally, the particle sizes and the coatings thicknesses used in carrying out the present procedure are at the lower ends of the particle size and coating thickness ranges disclosed in Fox et al. and may be even smaller than the smallest particle sizes and the smallest coating thicknesses disclosed in that reference. The particle sizes and coating thicknesses of the encapsulated sugar pellets are not critical for most applications of the present technique, as long as the particles are not so large as to become lodged in the arterial system AS of the tumor TM. Even then, the encapsulated sugar particles will dissolve more or less rapidly and thereby serve to implement the contemplated treatment process.

Figure 3:
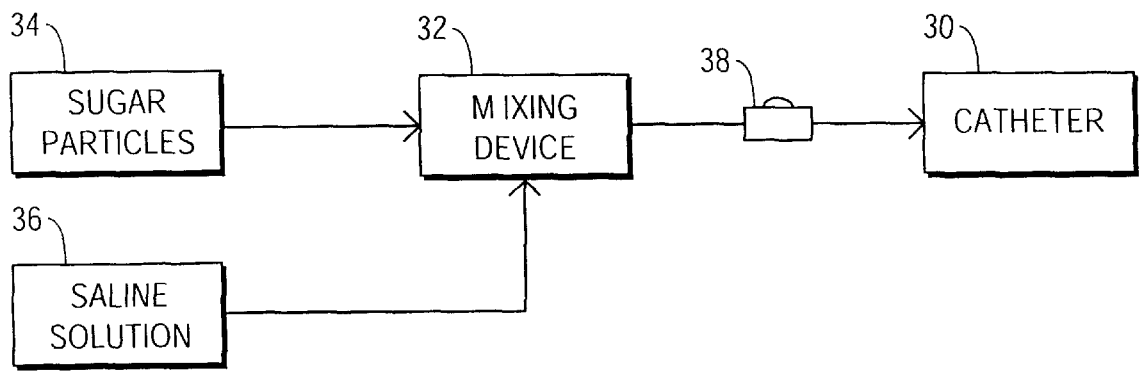
FIG. 3 is a block diagram of a system for carrying out a cancer treatment method in accordance with the present invention.

FIG. 3 depicts a system for implementing the tumor treatment method when a sclerosing agent such as sugar is conveyed in the form of time-release encapsulated particles to the site of a tumor TM. A catheter 30 partially inserted into the patient's vascular system VS is connected outside the patient PT to a mixing device 32 supplied by a sugar pellet source 34 and a saline reservoir 36. A flow regulator 38 is provided between mixing device 32 and catheter 30 for controlling the rate that a particle suspension from mixing device 32 is fed to the patient and particularly to the tumor TM to be destroyed.

As illustrated in FIG. 1, an alternative procedure for destroying tumor TM comprises inserting a tubular member 40 such as a cannula or a catheter directly into the tumor through overlying tissues including normal portions of organ IO. A sclerotic solution such as a 50% dextrose solution from reservoir 16 is dripped through tubular member 40 into tumor TM. The concentrated sugar eventually finds its way into the tumor's vascular system DVS and collapses the veins, thereby obstructing blood flow through the tumor.

In a modification of the above-described method for treating a cancerous growth, depicted in FIG. 4, a sclerotic solution is delivered to an upstream side of a tumor's blood supply or vascular system via a catheter 46 provided at a distal end with an inflatable balloon 54. Upon insertion of the catheter to the tumor TM, balloon 54 is inflated to occlude the artery AR feeding the tumor. A sclerosing solution is then delivered through catheter 46. In this case, the collapse of the tumor's vascular system DVS (FIG. 1) occurs primarily on the arterial side AS. Of course, this method is primarily effective if the target tumor TM has a limited number of readily identifiable and accessible arteries and if these feed arteries can be isolated so that other vital tissues of the patient are not affected. All of the arteries supplying the tumor TM are closed off in sequence, thereby destroying the tumor's blood supply and consequently the tumor itself It is to be noted that this procedure using a balloon catheter to deliver a sclerosing agent to collapse or obstruct a blood vessel may be used for other purposes other than destroying a tumor, for example, to selectively destroy varicose veins. In a recently proposed coronary artery by-pass procedure, a blood flow route is created around a coronary blockage through an adjacent coronary vein. The upstream and downstream sides of the by-pass route in the vein are closed by permanently implanted balloons. This procedure may be improved by injecting a sclerosing solution to permanently close off the vein on the opposite sides of the bypass route. There is no need then to implant balloons, which may slip, deflate or otherwise cease performing their blocking function.

The sclerosing procedure described hereinabove may be combined with other kinds of treatment which include the introduction of toxic substances into the body. For example, an alcohol such as methyl alcohol or arsenic may be delivered to the body of the tumor for selective absorption into cancer cells.

In an alternative procedure, a catheter is inserted through the patient's vascular system PVS until the tip of the catheter is located proximately to the tumor TM. The lumen of the catheter is coated with a layer of crystalline dextrose or other sugar. A second, smaller catheter is inserted inside the first catheter, either before or after deployment of the first catheter. The distal tip of the inner catheter is staggered in a distal direction from the distal tip of the outer catheter. An aqueous or saline solution is then fed through the inner catheter at a predetermined rate. This solution dissolves the sugar layer deposited along an inner surface of the outer catheter. This dissolution inside the other catheter generates a highly concentrated sugar solution which is delivered from distal tip of the outer catheter into the arterial supply AS of the tumor TM. After a period of time in which a sugar layer portion originally disposed between the distal tip of the inner catheter and the distal tip of the outer catheter essentially completely dissolves, the inner catheter is withdrawn a predetermined distance from the outer catheter (and the patient) to uncover another portion of the sugar layer. In a continuing treatment of the tumor, an aqueous or saline solution is fed through the inner catheter, gradually dissolving another portion of the sugar layer.

In yet another alternative procedure, after deployment of a catheter so that a tip thereof is disposed in artery AR of the tumor TM, a sugar rod is inserted into the catheter from outside the patient. The sugar rod is pushed through the catheter by a wire push rod until a far end of the sugar rod enters artery AR, where it dissolves in the arterial flow. The sugar rod is pushed out of the catheter at a rate resulting in a desired concentration of sugar in the artery AR. Of course, the sugar rod may fragment during its excursion through the catheter. However, this will have only a minor effect on the rate that concentrated sugar enters the arterial blood supply AS of the tumor TM.

Although the invention has been described in terms of particular embodiments and applications, one of ordinary skill in the art, in light of this teaching, can generate additional embodiments and modifications without departing from the spirit of or exceeding the scope of the claimed invention. Other known sclerotic agents besides a concentrated sugar solution can be used in carrying out the method of the present invention. For example, 5% quinine and urea hydrochloride solution. Preferably, the sclerotic agent is a natural substance which is generally nontoxic and biocompatible. A sugar such as dextrose is such a substance.

As discussed herein, catheter 12 is inserted from the upstream side, i.e., through arteries of the patient vascular system VS, so that the distal end of the catheter is disposed near the tumor TM, in an artery AR supplying the tumor. This procedure is preferred because of the usual reasons. For example, the valves in the veins of the vascular system interfere with insertion of a catheter. In addition, the desired sclerotic effect is more easily confined to the tumor's dedicated vascular system DVS when the sclerosing agent is fed to the arterial supply AS of the tumor. There may be situations, however, where catheterization from a downstream side is preferred.

Where a sclerosing agent such as sugar is conveyed in the form of time-release encapsulated particles to the site of a tumor TM, the coating may be a gelatinous or other composition which naturally melts at body temperature or slightly below body temperature, such as at about 90° F. Thus, the encapsulated sugar particles maintain their integrity until they enter the blood or a downstream portion of the delivery catheter or tube which is equilibrated to body temperature. Alternatively, the coating material can disintegrate at a temperature higher than body temperature. In that case, the delivery catheter and particularly the downstream end thereof is provided with heating elements as described in U.S. Pat. No. 5,260,020, for elevating the temperature of the sclerosing suspension so that the sugar is released from its encapsulated form and dissolves in solution to create a highly concentrated sugar solution.

Accordingly it is to be understood that the drawings and descriptions herein are proffered by way of example to facilitate comprehension of the invention and should not be construed to limit the scope thereof.

What is claimed is:

1. A method for treating cancer, comprising:
    inserting a tube into a patient, so that a distal end of said tube is disposed proximately to a tumor; and
    feeding a sclerosing agent including a sugar through said tube into the patient and into the tumor.

2. The method defined in claim 1 wherein said tube is a catheter, the inserting of said catheter including the step of guiding said catheter through a vascular system of the patient so that a distal tip of said catheter is disposed proximately to the tumor in an artery supplying the tumor.

3. The method defined in claim 2 wherein said sugar is introduced into said catheter in a form for inhibiting adherence of sugar to an inner surface of said catheter.

4. The method defined in claim 3 wherein said sugar is introduced into said catheter in the form of pellets with time release outer coatings.

5. The method defined in claim 4 wherein said sugar is introduced into said catheter in the form of pellets which are hard throughout.

6. The method defined in claim 3 wherein said sugar is introduced into said catheter in a form which dissolves at a predetermined rate in body fluids.

7. The method defined in claim 6 wherein said catheter is provided with means for heating at least a distal end portion of said catheter, thereby facilitating dissolving of the sugar in blood fluids.

8. The method defined in claim 2 wherein said catheter is provided with means for heating said catheter, further comprising the step of operating said means for heating during feeding of said sclerosing agent through said catheter, thereby inhibiting adhesion of sugar to an inner surface or lumen of said catheter.

9. The method defined in claim 8 wherein said means for heating includes a wire obturator disposed inside said catheter.

10. The method defined in claim 2, further comprising the steps of inserting a wire obturator periodically into said catheter and conducting electrical current through said obturator to heat said obturator and clear sugar deposits from a lumen of said catheter.

11. The method defined in claim 2, further comprising inflating a balloon at a distal tip of said catheter after disposition of said distal tip proximately to said tumor and prior to feeding of said sclerosing agent through said catheter.

12. The method defined in claim 1 wherein the inserting of said tube includes inserting said tube through overlying organs and directly into the tumor.

13. The method defined in claim 12 wherein said sugar is introduced into said tube in a form for inhibiting adherence of sugar to an inner surface of said tube.

14. The method defined in claim 13 wherein said sugar is introduced into said tube in the form of pellets with hardened outer surfaces.

15. The method defined in claim 14 wherein said sugar is introduced into said tube in the form of pellets which are hard throughout.

16. The method defined in claim 12 wherein said sugar is introduced into said tube in a form which dissolves at a predetermined rate in body fluids.

17. The method defined in claim 15 wherein said catheter is provided with means for heating at least a distal end portion of said catheter, thereby facilitating dissolving of the sugar in blood fluids.

18. The method defined in claim 12 wherein said tube is provided with means for heating at least a distal end portion of said tube, thereby inhibiting adhesion of sugar to an inner surface or lumen of said tube.

19. The method defined in claim 1, further comprising the step of delivering a vasoconstrictive agent to a venous system for said tumor.

20. The method defined in claim 19 wherein said vasoconstrictive agent is delivered to the venous system of the tumor substantially simultaneously with the feeding of said sclerosing agent into the tumor.

21. The method defined in claim 20 wherein said vasoconstrictive agent is taken from the group consisting essentially of caffeine and nicotine.

22. The method defined in claim 1 wherein said sclerosing agent is fed into the tumor at an elevated temperature.

23. The method defined in claim 1 wherein the tumor has a substantially dedicated venous system, the feeding of said sclerosing agent includes the step of sclerosing all of the veins of the tumor's venous system.

* * * * *